US009008270B2

(12) United States Patent
Hasegawa et al.

(10) Patent No.: US 9,008,270 B2
(45) Date of Patent: Apr. 14, 2015

(54) SAMPLE COOLING APPARATUS FOR X-RAY DIFFRACTOMETER AND X-RAY DIFFRACTOMETER

(75) Inventors: Tomokazu Hasegawa, Ome (JP); Kazuaki Aburaya, Hamura (JP)

(73) Assignee: Rigaku Corporation, Akishima-Shi, Tokyo (JP)

( * ) Notice: Subject to any disclaimer, the term of this patent is extended or adjusted under 35 U.S.C. 154(b) by 469 days.

(21) Appl. No.: 13/454,393

(22) Filed: Apr. 24, 2012

(65) Prior Publication Data

US 2012/0275567 A1 Nov. 1, 2012

(30) Foreign Application Priority Data

Apr. 26, 2011 (JP) ................ 2011-098825

(51) Int. Cl.
*G01N 23/207* (2006.01)
*H05G 1/02* (2006.01)
*G01N 1/42* (2006.01)

(52) U.S. Cl.
CPC ............... *G01N 23/207* (2013.01); *G01N 1/42* (2013.01); *G01N 2223/307* (2013.01)

(58) Field of Classification Search
CPC ........................................................ G01N 1/42
USPC .................................................... 378/79–81
See application file for complete search history.

(56) References Cited

U.S. PATENT DOCUMENTS

| 6,408,047 B1* | 6/2002 | Kitagawa et al. ............... 378/79 |
| 7,274,769 B2* | 9/2007 | Nordmeyer et al. ........... 378/80 |
| 2009/0133410 A1* | 5/2009 | Thorne et al. ..................... 62/62 |

FOREIGN PATENT DOCUMENTS

JP          9-22984 A          9/1997

* cited by examiner

*Primary Examiner* — David J Makiya
*Assistant Examiner* — Danielle Fox
(74) *Attorney, Agent, or Firm* — BUchanan Ingersoll & Rooney PC

(57) ABSTRACT

The sample cooling apparatus is used in an X-ray diffractometer for rotating a sample supported by a sample rod about an ω axis, directing X-rays thereto, and detecting X-rays deflected from the sample using an X-ray detector. The apparatus has a nozzle for blowing a cooling gas on the sample; and a gas-suctioning device for suctioning, via an aperture, gas that has passed over the sample. The sample rod moves when rotated about the ω axis forming a conical surface having the sample as a vertex. The nozzle is provided so that the extension direction of the sample rod and the direction of the blown gas form an acute angle of 90° or less. The gas-suctioning device suctions the gas so the path of gas having contacted the sample rod bends when the extension direction of the sample rod and the blown direction of the gas form an acute angle.

14 Claims, 11 Drawing Sheets

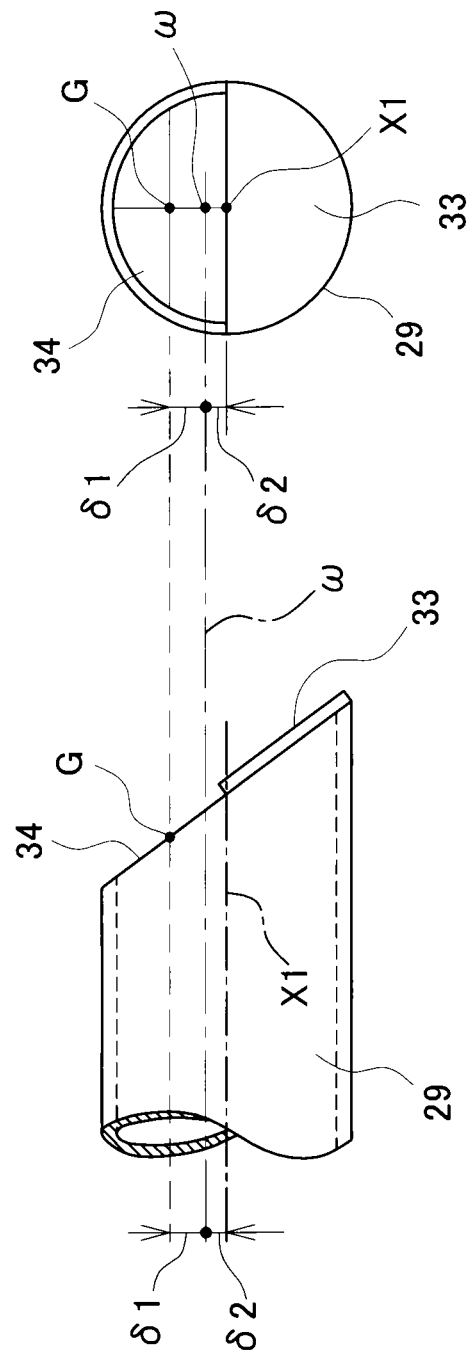

US 9,008,270 B2

SAMPLE COOLING APPARATUS FOR X-RAY DIFFRACTOMETER AND X-RAY DIFFRACTOMETER

BACKGROUND OF THE INVENTION

1. Field of the Invention

The present invention relates to a sample cooling apparatus used in an X-ray diffractometer and to an X-ray diffractometer that uses the sample cooling apparatus.

2. Description of the Related Art

An X-ray diffractometer performs measurement in which X-rays are directed to a sample and the X-rays coming away from the sample are detected by an X-ray detector. It is sometimes necessary to cool the sample during this measurement. During structural analysis of a single crystal, for example, in order to stabilize the molecular structure in the single crystal sample and obtain highly reliable data, measurement is sometimes performed while a low-temperature gas, e.g., nitrogen gas at about 93 K (−180° C.) to 143 K (−130° C.), is blown onto the sample.

Patent Citation 1, for example, discloses a sample cooling apparatus for an X-ray diffractometer. In the sample cooling apparatus described in this reference, a sample-supporting component such as a glass rod or the like extends in the up-down direction within a space, and a sample is supported on a distal end of the sample-supporting component. Measurement is performed while the angle at which X-rays impinge on the sample is changed by rotating the sample about an ω axis extending in the vertical up-down direction. A gas-blowing nozzle is disposed above the sample, and the sample is cooled by low-temperature gas discharged from the nozzle during measurement.

In this conventional apparatus, the sample-supporting component is mounted on an arc stage, and through use of this arc stage, the sample-supporting component can be inclined in relation to the vertical direction while the sample remains in position on the ω axis. When the sample is rotated about the ω axis with the sample-supporting component in this inclined state, the sample-supporting component moves in rotation so as to describe a cone with the sample at the vertex thereof. A gas discharge vent of the gas-blowing nozzle is disposed above a conical movement surface described by the sample-supporting component.

FIG. 11 shows another conventional example of a sample cooling apparatus for an X-ray diffractometer. In this conventional apparatus, a sample rod 101 supporting a sample S is supported in an inclined state by an ω rotation substrate 102. When the ω rotation substrate 102 is rotated about the ω axis in order to change the incidence angle of an X-ray R1 incident on the sample S, and the sample S is rotated about the ω axis in the same manner, the sample rod 101 describes a conical surface having the sample S at the vertex thereof. A gas discharge vent 103a of a nozzle 103 for blowing low-temperature gas onto the sample S is disposed above the conical surface.

When low-temperature gas is blown onto a sample, there is usually a risk of ice forming on the sample and the sample support. However, in the conventional X-ray diffractometer described in Patent Citation 1 and shown in FIG. 11, the occurrence of ice is kept extremely low, and ice does not interfere with measurement by the X-ray diffractometer.

In the X-ray diffractometer described in Patent Citation 1 and shown in FIG. 11, the ω axis is set so as to extend in the up-down direction. Due to the need to use a power transmission mechanism that includes, for example, a worm and a large-diameter worm wheel as the mechanism for rotating the sample about the ω axis, a large space is often needed in the direction at a right angle to the cω axis. The shape of the X-ray diffractometer described in Patent Citation 1 and shown in FIG. 11 in the horizontal direction (i.e., the transverse direction) is therefore enlarged, and a large space must therefore be reserved for installation thereof.

As a result of research aimed at reducing the space needed for installing the X-ray diffractometer, the inventors discovered that the size of the installation space for the X-ray diffractometer in the horizontal direction can be reduced by changing the installation position of the ω rotation substrate 102 in FIG. 11, for example, from the horizontal position to the vertical position as indicated by the arrow Q, i.e., by setting the installation position of the ω rotation substrate 102 so that the ω axis extends in the horizontal direction.

PRIOR ART CITATIONS

[Patent Citation 1] Japanese Laid-open Patent Publication No. 9-229834

SUMMARY OF THE INVENTION

However, the inventors also discovered that when the ω rotation substrate 102 is placed in the vertical direction, i.e., the longitudinal direction, and X-ray analysis is carried out while blowing low-temperature gas onto the sample from the nozzle, the problem of ice formation on the sample and sample rod intensifies, and the reliability of the measurement is reduced.

The inventors made the following discovery as a result of investigating a way to overcome this problem of ice formation. Specifically, when the ω rotation substrate is set in advance to the longitudinal direction (i.e., when the ω axis is set to the horizontal direction), and the direction in which gas is blown from the nozzle or other gas discharge means is set so that gas is blown downward from above in the manner of the conventional technique, when the sample is rotated about the ω axis, the direction in which the sample-supporting component extends and the direction in which the low-temperature gas is blown are in an acute-angle state (state of being at an angle of less than 90 degrees from each other) or an obtuse-angle state (state of being at an angle of greater than 90 degrees from each other), and ice formation is severe particularly when the direction in which the sample-supporting component extends and the direction in which the low-temperature gas is blown are in an acute-angle state.

(Objects of the Invention)

The present invention was developed on the basis of the discovery described above, and an object of the present invention is to provide a sample cooling apparatus capable of effectively overcoming the problem of ice formation on the sample and sample-supporting component in an X-ray diffractometer in which the direction in which the sample-supporting component extends and the direction in which low-temperature gas is blown form an acute-angle state.

(Configuration of the Invention)

The sample cooling apparatus for an X-ray diffractometer according to the present invention is a sample cooling apparatus for cooling a sample, the apparatus being used in an X-ray diffractometer for rotating, about an ω axis, a sample supported by a sample-supporting component, changing an angle at which X-rays impinge on the sample, directing X-rays on the sample, and detecting X-rays coming away from the sample using an X-ray detector, the sample cooling apparatus of an X-ray diffractometer comprising: cooling-gas-blowing means for blowing a cooling gas on the sample;

and gas-suctioning means for suctioning, via an aperture, gas that has passed over the sample; wherein the sample-supporting component moves when rotated about the ω axis so as to form a conical surface having the sample as a vertex; the cooling-gas-blowing means is provided so that the direction in which the sample-supporting component extends and the direction in which gas is blown by the cooling-gas-blowing means form a state of being an acute angle of equal to or less than 90 degree; and the gas-suctioning means suctions the gas so that a path of the gas having contacted the sample-supporting component bends when the direction in which the sample-supporting component extends and the direction in which gas is blown by the cooling-gas-blowing means form the acute-angle state.

In the sample cooling apparatus of the present invention, the sample-supporting component rotates about the ω axis so as to describe a conical surface. The cooling-gas-blowing means is provided so that the direction in which the sample-supporting component extends and the direction in which gas is blown by the cooling-gas-blowing means form a state of being an acute angle of equal to or less than 90° when the ω angle of the sample-supporting means about the ω axis is a specific angle (e.g., between 0°, which is horizontal, and 90°, which is vertical).

When the direction in which the sample-supporting component extends and the direction in which gas is blown from the cooling-gas-blowing means are in the acute-angle state of 90° or less, a situation occurs in which the gas discharged from the cooling-gas-blowing means contacts the sample after contacting the sample-supporting component. In this case, there is a risk of ice forming on and around the sample due to the effect of turbulence on the downstream side of the sample-supporting component.

However, in the sample cooling apparatus of the present invention, since an aperture for gas suctioning is provided in the vicinity of the sample, and the gas flow that has passed over the sample-supporting component is immediately suctioned, turbulence is suppressed, and any turbulence that does occur can be immediately separated from the sample. As a result, ice can be prevented from forming on and adhering to the sample.

In the X-ray diffractometer according to the present invention, ice can be prevented from ever adhering, and accurate diffraction data can be obtained even when the ω axis is horizontally set and gas is blown from the cooling-gas-blowing means in the top-to-bottom direction. Enabling the ω axis to be set so as to extend in the horizontal direction makes it possible to reduce the length of the X-ray diffractometer in the horizontal direction and reduce the size of the installation space.

In the sample cooling apparatus for an X-ray diffractometer according to the present invention, the gas-suctioning aperture of the gas-suctioning means may integrally rotate about the ω axis together with the sample. Through this configuration, the aperture and the sample do not move relative to each other, and the component forming the aperture can therefore be prevented from striking the mechanism for supporting the sample. The aperture can also be brought closer to the sample.

In the sample cooling apparatus for an X-ray diffractometer according to the present invention, the aperture may be formed at a distal end of a tubular component; and the central axis of the tubular component may extend parallel to the ω axis. Since the length of the tubular component can be increased and the cross-sectional shape thereof reduced in size, the aperture can be brought close to the sample even when there is minimal space around the sample.

In the sample cooling apparatus for an X-ray diffractometer according to the present invention, the distal end of the tubular component preferably has an incline that follows the direction in which the sample-supporting component extends. Through this configuration, since the aperture is parallel to the sample-supporting component, the potential for turbulence occurring downstream from the sample-supporting component is reduced. Turbulence that does occur is also easily overcome.

In the sample cooling apparatus for an X-ray diffractometer according to the present invention, preferably, the aperture is formed at a distal end surface of the tubular component; a guide plate is attached to the distal end of the tubular component; the center of the aperture is disposed eccentrically with respect to the ω axis; and the guide plate is connected to the aperture. Here, the center of the aperture is the center thereof in the up-down direction and in the left-right direction.

By disposing the center of the aperture eccentrically with respect to the ω axis as described above, the position and area of the aperture with respect to the sample can be adjusted to create an optimal state in which turbulence does not occur, or in which turbulence that does occur can be immediately overcome. Providing the guide plate makes it possible to suppress turbulence.

In the sample cooling apparatus for an X-ray diffractometer according to the present invention, preferably, the aperture is formed on a portion of a distal end surface of the tubular component; a portion of the distal end surface of the tubular component other than the aperture is a guide plate; and the center of the aperture is disposed eccentrically with respect to the ω axis.

By disposing the center of the aperture eccentrically with respect to the ω axis, the position and area of the aperture with respect to the sample can be adjusted to create an optimal state in which turbulence does not occur, or in which turbulence that does occur can be immediately overcome. Providing the guide plate makes it possible to suppress turbulence.

In the case that the center of the aperture is eccentrically disposed with respect to the ω axis, it is preferred that the center of the aperture be eccentrically disposed toward the sample-supporting component location side of the ω axis. The wide portion of the aperture can thereby be made to face the sample-supporting component.

The sample cooling apparatus for an X-ray diffractometer according to the present invention may comprise an ω rotation substrate on which the sample-supporting component is supported, the substrate rotating integrally with the sample-supporting component about the ω axis. The gas-suctioning means may have a gas-suctioning part integrally provided to the tubular component; and an attachment structure by which the mutually integrated tubular component and gas-suctioning part are detachably attached to the ω rotation substrate. Through this configuration, the sample cooling apparatus of the present invention can easily be installed in an existing X-ray diffractometer.

In the sample cooling apparatus for an X-ray diffractometer according to the present invention, preferably, the ω axis extends in a horizontal direction; and the direction in which gas is blown by the gas-blowing means is a direction oriented downward from above. Setting the ω axis in the horizontal direction makes it possible to reduce the horizontally directed length of the drive system for rotating the sample or other components about the ω axis, and to facilitate a reduction in size of the X-ray diffractometer.

In the sample cooling apparatus for an X-ray diffractometer according to the present invention, preferably, the X-ray diffractometer has an ω-axis drive system for causing the sample to rotate about the ω axis; and a φ-axis drive system for causing the sample-supporting component to rotate about a central axis (φ axis) thereof; the impingement angle at which X-rays impinge on the sample is continuously caused to oscillate and change by the ω-axis drive system; the sample is rotated in a stepwise manner by the φ-axis drive system; and X-rays are made to impinge on the sample in individual X-ray impingement angle positions and in individual angular positions around the φ axis, and X-rays coming away from the sample are detected by the X-ray detector.

This configuration specifies a configuration for the X-ray diffractometer that is suitable for single crystal structural analysis. Since a single crystal sample must be cooled during measurement, data that are highly reliable can be obtained for a single crystal sample by applying the present invention to an X-ray diffractometer configured such as described above.

The X-ray diffractometer according to the present invention is an X-ray diffractometer for rotating, about an ω axis, a sample supported by a sample-supporting component, changing an angle at which X-rays impinge on the sample, directing X-rays on the sample, and detecting X-rays coming away from the sample using an X-ray detector; the X-ray diffractometer comprising the sample-cooling apparatus configured as described above.

In the X-ray diffractometer according to the present invention, ice can be prevented from ever adhering, and accurate diffraction data can be obtained even when the ω axis is horizontally set and gas is blown from the cooling-gas-blowing means in the top-to-bottom direction. Enabling the ω axis to be set so as to extend in the horizontal direction makes it possible to reduce the length of the X-ray diffractometer in the horizontal direction and reduce the size of the installation space.

BRIEF DESCRIPTION OF THE DRAWINGS

FIG. 3A is a side view showing a detailed view of the tubular component and aperture as main components of FIG. 2;

FIG. 3B is a front view of FIG. 3A;

DESCRIPTION OF THE PREFERRED EMBODIMENTS (First Embodiment of the X-ray Diffractometer and Sample Cooling Apparatus)

The X-ray diffractometer and sample cooling apparatus of the present invention will next be described on the basis of an embodiment. The present invention is, of course, not limited to this embodiment. The drawings are referred to in the following description, but constituent elements are sometimes shown at a scale other than the actual scale thereof in order to facilitate understanding of characteristic portions.

Figure 1:
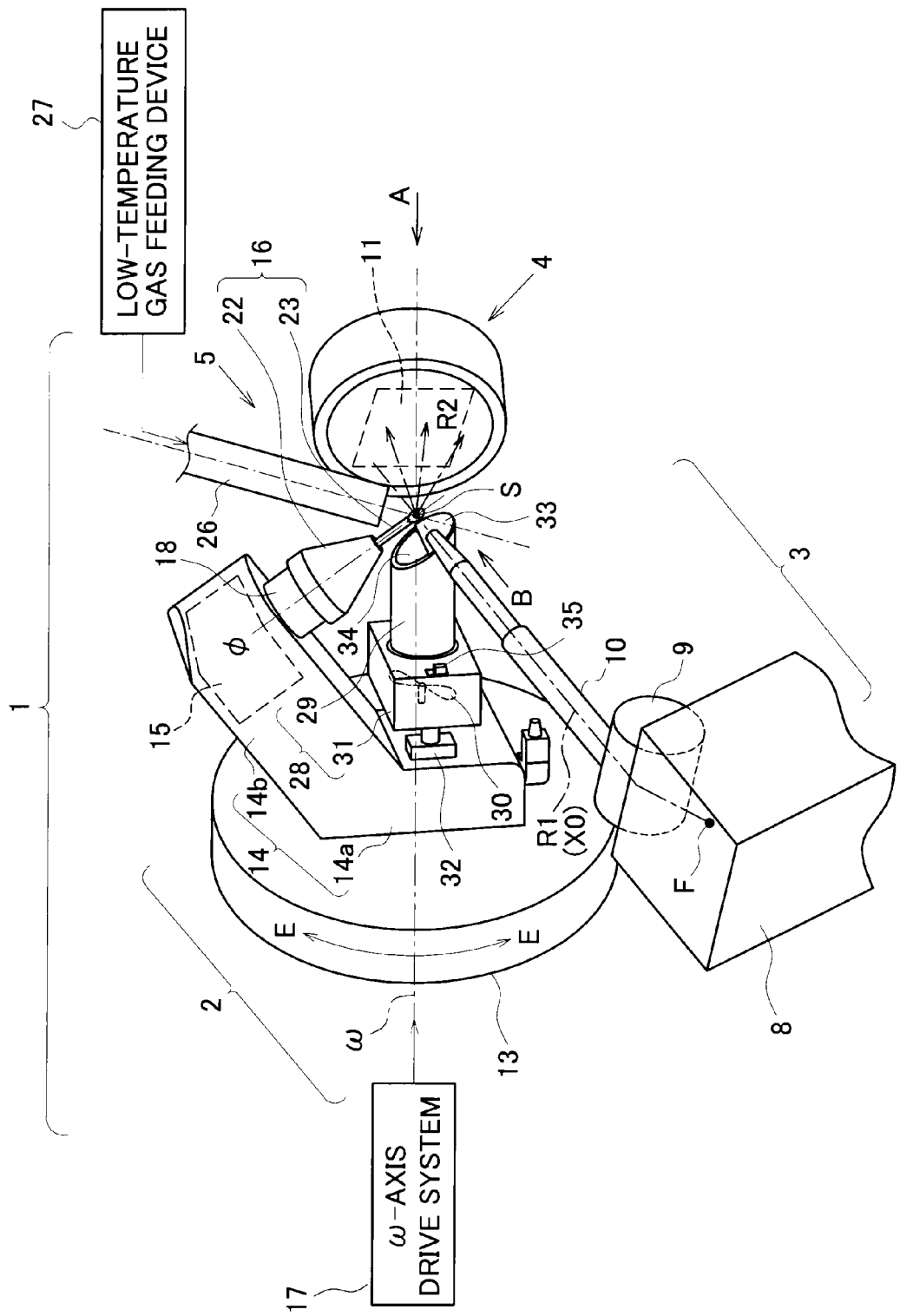
FIG. 1 is a perspective view showing an embodiment of the X-ray diffractometer and of the sample cooling apparatus of the present invention.
Figure 2:
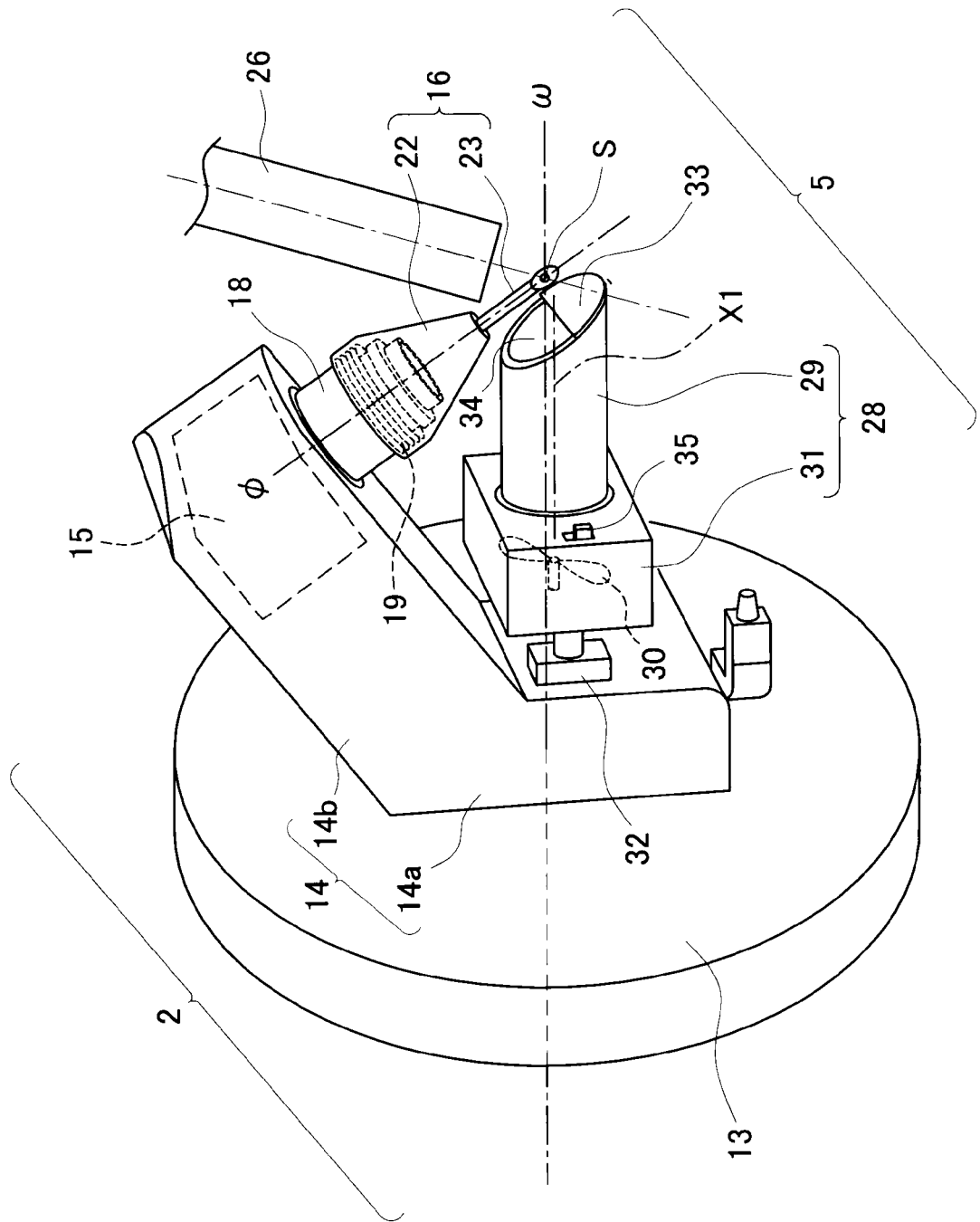
FIG. 2 is a perspective view showing an embodiment of the sample support system and sample cooling apparatus as main components of the X-ray diffractometer shown in FIG. 1.

FIG. 1 shows an embodiment of the X-ray diffractometer according to the present invention. FIG. 2 shows the main components of the X-ray diffractometer. In these drawings, the X-ray diffractometer 1 of the present embodiment is used primarily for structural analysis of a single crystal sample. The X-ray diffractometer 1 has a sample support system 2 for supporting a sample S; an incidence optical system 3 for directing X-rays to the sample S; a light-receiving system 4 for detecting X-rays coming away from the sample S; and a sample cooling apparatus 5 for blowing and suctioning, toward the sample S, a low-temperature gas for cooling the sample S.

(Incidence Optical System)

The incidence optical system 3 has an X-ray generation device 8 provided with an X-ray source F; a monochromator 9 for monochromatizing the X-rays generated by the X-ray source F; and a collimator 10 for forming the X-rays monochromatized by the monochromator 9 into a parallel beam. The X-ray source F has, for example, a filament for generating thermoelectrons when electrified, and a target on which the thermoelectrons impinge. The region on the target on which the thermoelectrons impinge is an X-ray focal point, and X-rays are generated from this X-ray focal point.

The monochromator 9 is formed by a crystal monochromator, for example. The collimator 10 is formed by a pinhole collimator, for example, which parallelizes X-rays through use of a plurality of pinholes. By the configuration described above, X-rays R1 from the X-ray source F are incident on the sample S after being monochromatized by the monochromator 9 and parallelized by the collimator 10. The central axis of the incident X-rays R1 is referred to hereinafter as the X-ray optical axis X0.

(Light-receiving system)

The light-receiving system 4 is composed of, including, a two-dimensional X-ray detector 11 which uses a CCD X-ray sensor. A CCD is a charge coupled device. The two-dimensional X-ray detector 11 detects X-rays emitted from the sample S, i.e., diffracted X-rays R2, in two dimensions (i.e., in a plane), and detects X-ray intensity together with in-plane position information.

(Sample Support System)

The sample support system 2 has an ω rotation substrate 13, an arm component 14 fixed on a surface of the ω rotation substrate 13, a φ-axis drive system 15 provided inside the arm component 14 at a distal end portion thereof, and a sample support 16 for supporting the sample S. The ω rotation substrate 13 is formed in a disc shape and is driven by an ω-axis drive system 17 so as to rotate about the ω axis. The ω axis extends in the horizontal direction. However, a range of error with respect to the horizontal direction is allowed in the ω axis insofar as X-ray measurement is unaffected. The ω axis passes through the center of a circular surface of the ω rotation substrate 13 and is orthogonal to the circular surface.

The ω-axis drive system 17 includes a worm and a large-diameter worm wheel, for example. When the large-diameter worm wheel is placed in a horizontal orientation, the width of the X-ray diffractometer 1 in the transverse direction increases, and a large amount of space is needed for installation. The present embodiment, however, is more practical because the large-diameter worm wheel can be placed in a vertical orientation, and the installation space in the width direction can be reduced. The arm component 14 is formed in a bent shape formed by a base part 14a fixed to a surface of the ω rotation substrate 13, and a protruding part 14b which protrudes forward at an angle from the base part 14a. The φ-axis drive system 15 is provided inside the protruding part 14b in a distal end portion thereof.

In the φ-axis drive system 15, an output shaft 18 is rotated by an electric motor such as a pulse motor or a servo motor. The output shaft 18 protrudes outside the protruding part 14b of the arm component 14. As shown in FIG. 2, a helical screw or other structure for connection is provided at a distal end of the output shaft 18, and the sample support 16 is screwed on by this connecting structure. The sample support 16 has a base 22 and a sample rod 23 as a sample-supporting component provided at a distal end of the base 22.

The sample to be measured, which is a single crystal sample S in the present embodiment, is fixed to the distal end of the sample rod 23 by an adhesive or the like. A female screw fitted on a helical screw 19 provided to the output shaft 18 that protrudes from the arm component 14 is provided inside the base 22, and the base 22 is connected to the output shaft 18 of the φ-axis drive system 15 by the fitting together of the female screw and the helical screw 19. When the sample support 16 is connected to the output shaft 18 in the manner described above, the sample S at the distal end of the sample rod 23 is mounted on the ω axis, which is the central axis of rotation of the ω rotation substrate 13.

The base 22 may be composed of a single component, or may be a goniometer head, which is a mechanism which functions to move the sample rod 23. Examples of the function of this goniometer head include adjusting the height position of the sample rod, adjusting translational movement (movement in the xy plane) of the sample rod, adjusting the position of the sample rod in the arc direction, and other functions. These position adjustments are usually performed to align the center of the sample S with the center of measurement.

The φ-axis drive system 15 rotates the output shaft 18 about the φ axis, which is an axis passing through the center of each of the output shaft 18 and the sample rod 23. The φ axis also passes through the sample S, and when the output shaft 18 rotates, resulting in rotation of the sample rod 23, the sample S also accordingly rotates about the φ axis.

Figure 4A:
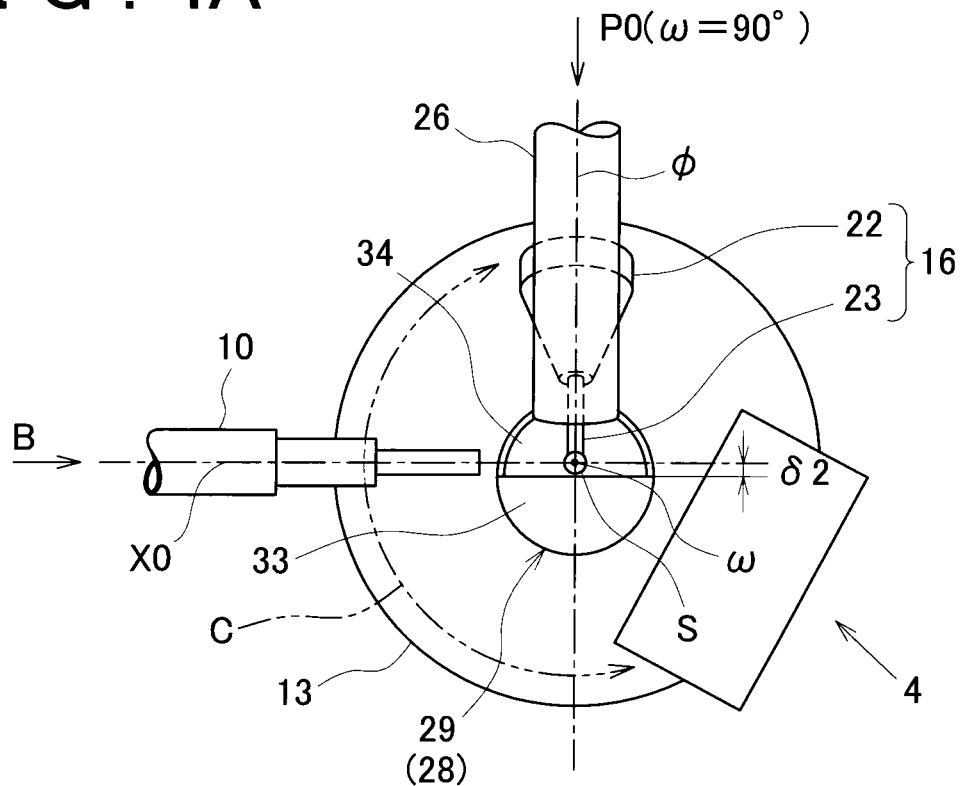
FIG. 4A is a partial front view showing the X-ray diffractometer from the direction of the arrow A in FIG. 1, and shows a state in which the sample support rod is at ω=90°.
Figure 4B:
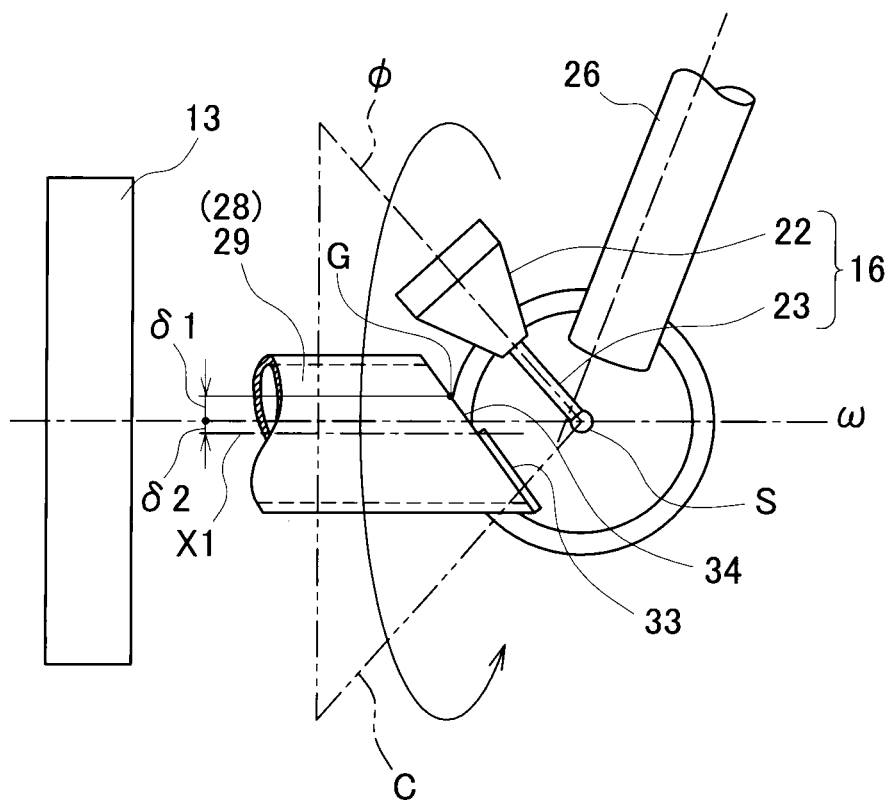
FIG. 4B is a side view from the direction of the arrow B in FIG. 4A.

FIG. 4A shows the configuration of the X-ray diffractometer 1 as viewed from the front from the direction of the arrow A in FIG. 1. FIG. 4B shows the configuration of the X-ray diffractometer 1 as viewed from the side from the direction of the arrow B in FIG. 1 and the arrow B in FIG. 4A. When the ω-axis drive system 17 in FIG. 1 activates and the ω rotation substrate 13 rotates about the ω axis as indicated by the arrow E-E, the sample rod 23 of the sample support 16 moves so as to describe a conical surface having the sample S at the vertex thereof, as indicated by the reference symbol C in FIGS. 4A and 4B. Specifically, the region of the sample support 16 that is movable about the ω axis is the region that extends from the upper position indicated by the reference P0 in FIG. 4A to the lower position indicated by the reference P2 in FIG. 6A, through the middle position indicated by the reference P1 in FIG. 5A. The conical surface C as the region through which the sample support 16 can move does not extend to the location of the light-receiving system 4.

Rotation of the sample S about the ω axis is referred to as ω rotation, and this rotation is performed in order to change the angle at which the X-rays R1 are incident on the sample S in FIG. 1. Rotation of the sample S about the φ axis is referred to as φ rotation, and this rotation is performed in order to change, in cooperation with the ω axis, the angle at which incident X-rays R1 are incident on the sample S.

(Sample Cooling Apparatus)

In FIG. 1, the sample cooling apparatus 5 has a discharge nozzle 26 as a cooling-gas-blowing means; a low-temperature gas feeding device 27 for feeding a low-temperature gas to the discharge nozzle 26; and a gas-suctioning device 28 as a gas-suctioning means. The discharge nozzle 26 discharges, i.e., ejects, the fed gas toward the sample S from a discharge vent at the lower end thereof. The low-temperature gas feeding device 27 may be configured so as to generate low-temperature nitrogen gas by heating liquid nitrogen with a heater, for example. Low-temperature gas at about 143 K (−130° C.), for example, can be supplied by this method.

The low-temperature gas feeding device 27 may also be configured so as to generate low-temperature nitrogen gas by using a cryocooler to heat-exchange nitrogen gas extracted from the atmosphere. This configuration is disclosed in Japanese Laid-open Patent Publication No. 8-278400, for example. By this method, low-temperature gas, for example, at about 93 K (−180° C.) can be supplied. A cooling method using He (helium) may also be employed in the low-temperature gas feeding device 27.

As shown in FIG. 2, the gas-suctioning device 28 has a component having a tubular shape (hereinafter referred to as a tubular component) 29, and a gas-suctioning part 31 which houses a fan 30. The tubular component 29 and the gas-suctioning part 31 are formed integrally with each other. An attachment structure 32 provided with a magnet is provided to a back surface of the gas-suctioning part 31, and the gas-suctioning device 28 is fixed by magnetism to a front surface of the base part 14a of the arm component 14 by the attachment structure 32. The tubular component 29 and the gas-suctioning part 31 may also be formed separately, i.e., as separate components.

Only one attachment structure 32 is shown in FIG. 2, but another attachment structure 32 having the same structure is actually provided on the inside in the horizontal direction, thus enabling the gas-suctioning device 28 to be securely fixed to the arm component 14. The number or positioning of the attachment structures 32 may, of course, be altered as needed. The attachment structure 32 is configured to use magnetic force in the present embodiment, but any other configuration may be adopted for the attachment structure 32.

The tubular component 29 is a cylinder, that is a tube having a circular cross section, in the present embodiment. The tubular component 29 may also be a tube having a square cross section, a tube having an elliptic cross section, a tube having a cross section of a rectangle with both ends rounded, or a tube having any other cross-sectional shape as needed. The front surface of the tubular component 29, i.e., the surface of the tubular component 29 that faces the sample S, is an inclined surface aligned with the extension direction of the sample rod 23. Here, "aligned with" means parallel to, or inclined so as to be nearly parallel. A guide plate 33 is also provided to the inclined front surface of the tubular component 29, and an aperture 34 is formed by the portion where the guide plate 33 is absent. In other words, the aperture 34 and the guide plate 33 constitute the front surface of the tubular component 29, and this front surface is inclined in alignment with the sample rod 23. The "guide plate" is a plate for guiding the gas flow.

The guide plate 33 occupies a region having half the area of the inclined front surface of the tubular component 29. In other words, the edge of the guide plate 33 toward the inside of the tube is adjacent to or in contact with the axial center $X1$ of the tubular component 29, as shown in FIGS. 3A and 3B. The center (i.e., the center in the up-down and left-right directions of the aperture 34) G of the aperture 34 is shifted by an offset amount 61 from the $\omega$ axis. In other words, the center G of the aperture 34 of the tubular component 29 is disposed eccentrically with respect to the $\omega$ axis. In the present embodiment, the axial center $X1$ of the tubular component 29 is shifted by an offset amount 62 (in the opposite direction from 61) from the $\omega$ axis. However, the axial center $X1$ may also coincide with the $\omega$ axis.

In FIG. 2, a starting switch 35 is provided to the front surface of the gas-suctioning part 31. When this switch 35 is turned on, the fan 30 of the gas-suctioning part 31 activates, and the air in the vicinity of the sample S is suctioned through the aperture 34.

The operation of the X-ray diffractometer 1 and sample cooling apparatus 5 configured as described above will next be described.

(Setup of the Apparatus)

In the case that measurement is performed with cooling applied, a user fixes the gas-suctioning device 28 to the base part 14a of the arm component 14 by using the attachment structure 32, and attaches the sample support 16, a sample S for measurement (single crystal sample S in the present embodiment) being attached to the distal end of the sample rod 23 thereof, to the output shaft 18 at the distal end of the arm component 14. The user also sets the discharge nozzle 26 so that the gas discharge vent at the distal end thereof is positioned in the vicinity of the sample S.

(Analysis for Single crystal Structural)

Figure 5A:
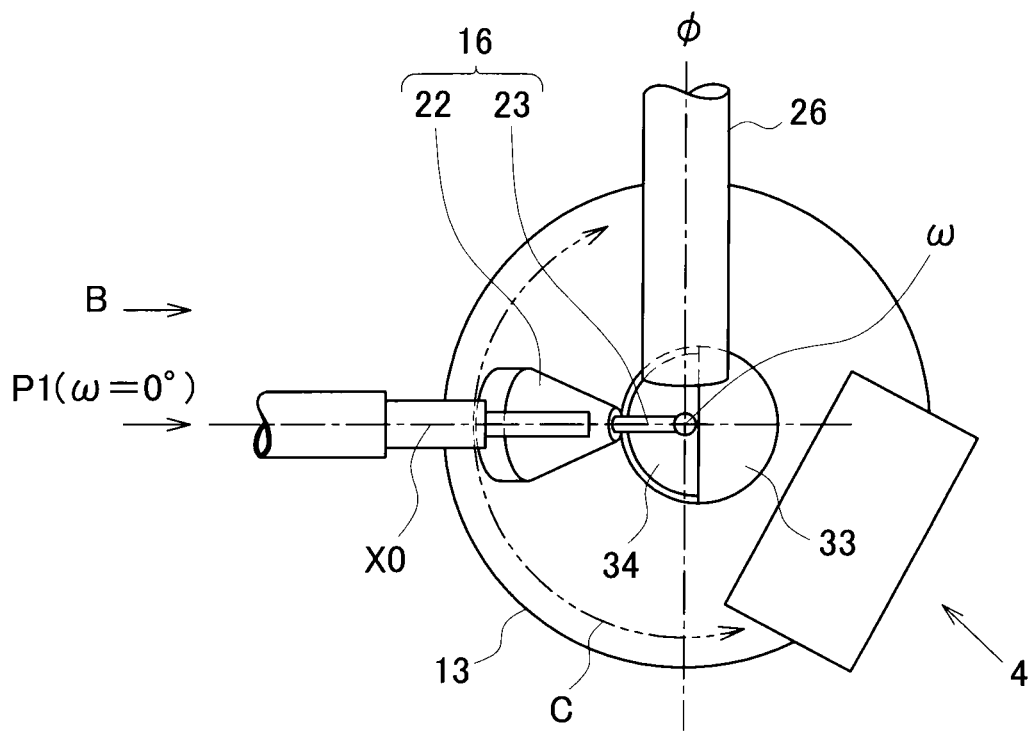
FIG. 5A is a partial front view showing the X-ray diffractometer from the direction of the arrow A in FIG. 1, and shows a state in which the sample support rod is at ω=0°.
Figure 5B:
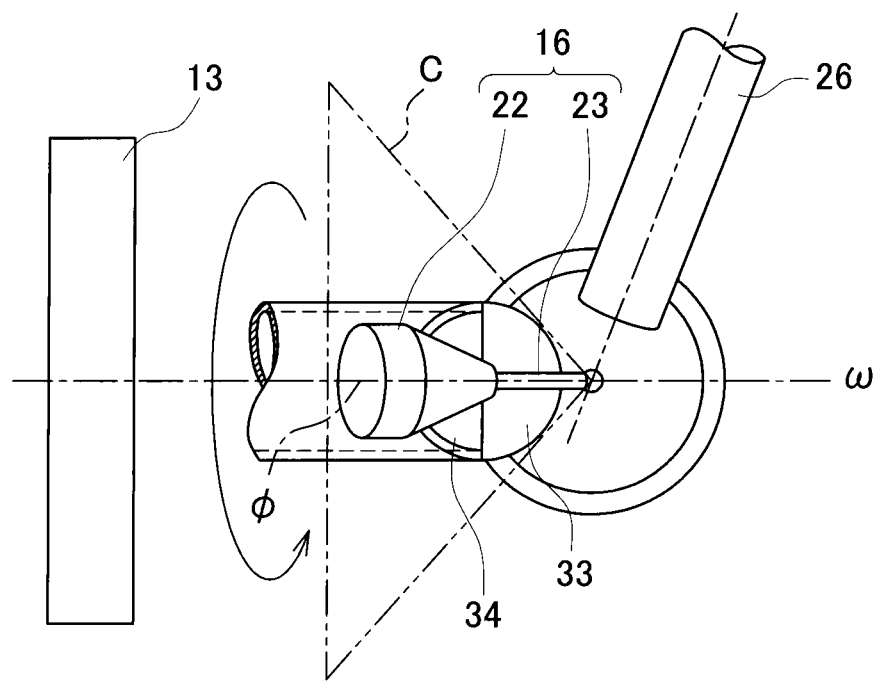
FIG. 5B is a side view from the direction of the arrow B in FIG. 5A.
Figure 6A:
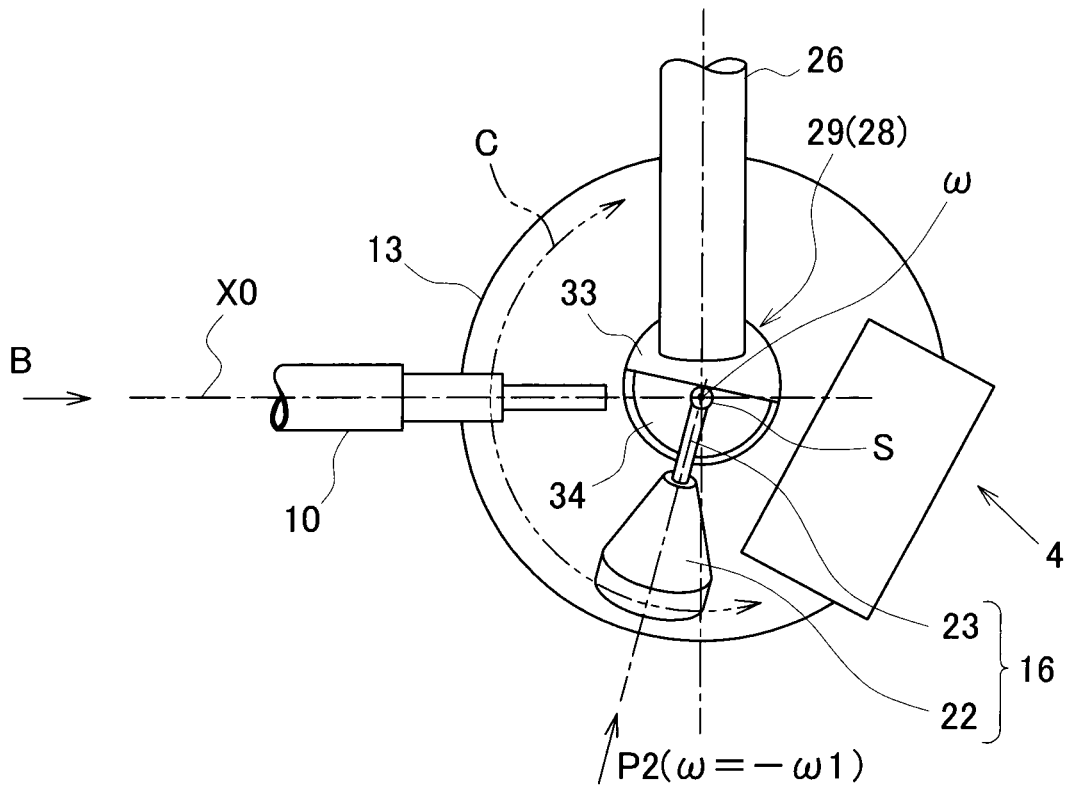
FIG. 6A is a partial front view showing the X-ray diffractometer from the direction of the arrow A in FIG. 1, and shows a state in which the sample support rod is at ω=−c1°.
Figure 6B:
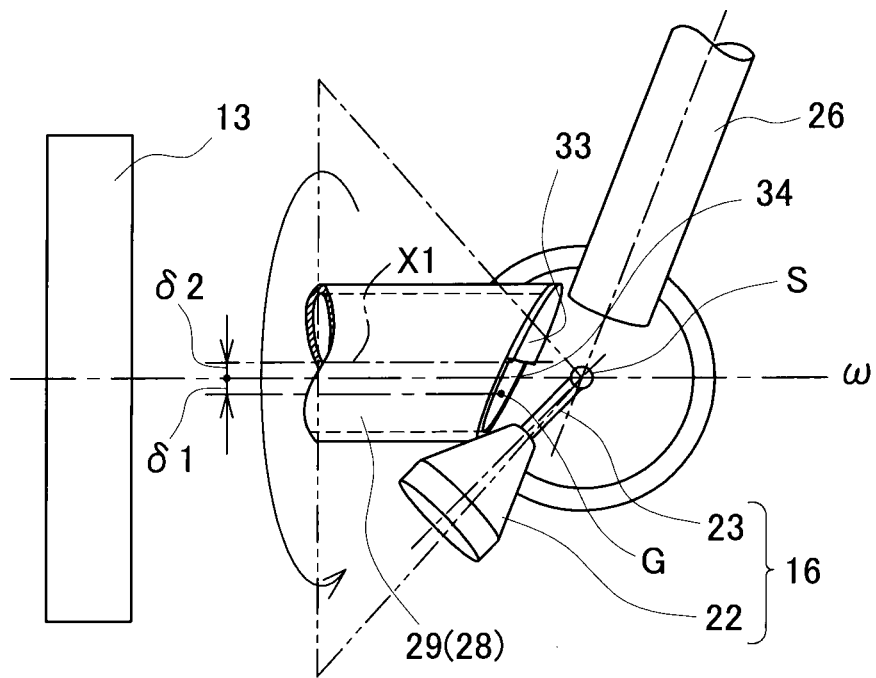
FIG. 6B is a side view from the direction of the arrow B in FIG. 6A.

In the present embodiment, $\omega=0°$ at position P1 where the sample rod 23 is aligned with the X-ray optical axis X0, as shown in FIG. 5A; $\omega=90°$ at position P0 where the sample rod 23 extends in the vertical direction, as shown in FIG. 4A; and $\omega=-\omega 1$ at position P2 where the sample rod 23 at the lowest position, as shown in FIG. 6A. After setting of the apparatus as described above is completed, the range of $\omega$ rotation in relation to the sample S is set according to the purpose of the measurement. In a normal apparatus, the angle $-\omega 1$ of the lowest position ranges from minus 70 degrees to about minus 75 degrees.

When the range of $\omega$ rotation is determined, the sample S is placed in a desired initial position within the $\omega$ angle range, and is also placed in an initial position for $\omega$ rotation. Low-temperature gas, e.g., nitrogen gas, is then produced from the low-temperature gas feeding device 27 shown in FIG. 1, and nitrogen gas is discharged toward the sample S from the discharge nozzle 26. The sample S is thereby set to the desired low temperature. Cooling the sample S to a low temperature makes it possible to stabilize the crystal structure in the sample, and a sharp, clear diffraction image can be obtained as a result. After the sample S is set to a predetermined low temperature, X-rays are emitted from the X-ray source F shown in FIG. 1, and X-rays that are monochromatized and parallelized are incident on the sample S.

When diffracted X-rays R2 are emitted from the sample S in accordance with the crystal structure within the sample S, the X-rays R2 are received by the CCD two-dimensional X-ray detector 11, and position data and intensity data of the diffracted X-rays are measured. During measurement, the $\phi$ angle is changed in stepwise fashion (incrementally), the $\omega$ angle is continuously changed in oscillating fashion at each $\phi$ angle, and data for the changed $\omega$ angles and $\phi$ angles are collected. Data are thereafter collected for each individual angle position in the $\omega$ angle range and $\phi$ angle range initially set.

(Cooling of the Sample)

In the present embodiment, when the sample S rotates from the upper position at $\omega=90°$ in FIG. 4A to the lower position at $\omega=-\omega 1$ in FIG. 6A, the tubular component 29 of the gas-suctioning device 28 rotates integrally with the sample support 16 about the $\omega$ axis through the action of the arm component 14. At this time, since the center G of the aperture 34 of the tubular component 29 is eccentric by an offset amount $\delta 1$ with respect to the $\omega$ axis (see FIGS. 3A, 3B), a more favorable gas flow can be achieved than when the center G of the aperture 34 coincides with the $\omega$ axis, as described below.

Figure 7:
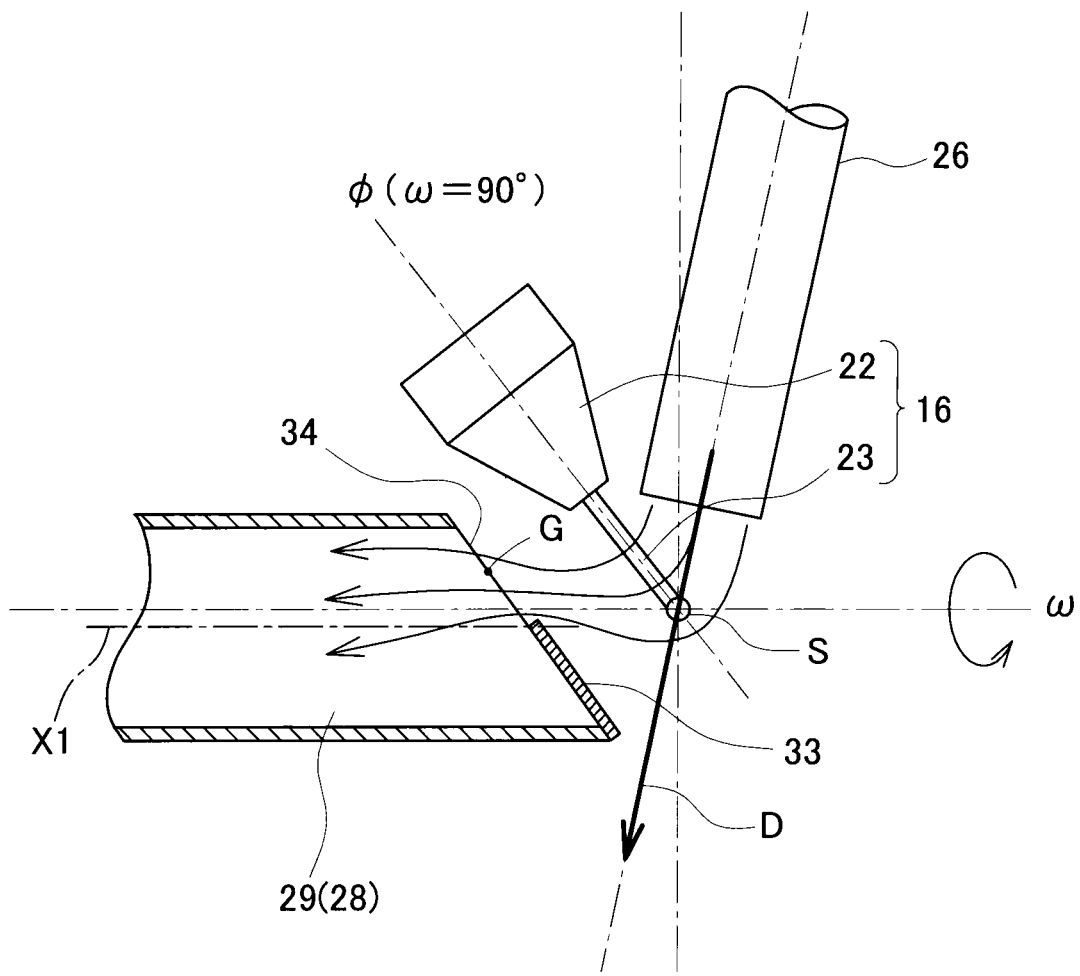
FIG. 7 is a schematic view showing state of flow of the cooling gas in the state (ω=90°) of FIG. 4B.

When the sample S and the sample rod 23 are positioned so that $\omega=90°$, as shown in FIG. 4A, the gas flowing from the discharge nozzle 26 and suctioned into the aperture 34 of the tubular component 29 of the gas-suctioning device 28 is as shown schematically in FIG. 7. Specifically, when $\omega=90°$, the sample rod 23 supporting the sample S enters the gas flow at a downward-sloping tilt. At this time, speaking of the plane at a right angle to the direction D in which gas is blown by the discharge nozzle 26, this plane touches the sample rod 23 before touching the sample S. In other words, the gas flow contacts the sample rod 23 before contacting the sample S.

When the gas flow contacts the sample rod 23 before contacting the sample S, turbulence occurs at a position downstream from the sample rod 23, and this turbulence causes ice to adhere to the sample S and to the interfacing portion between the sample S and the sample rod 23. In the present embodiment, however, when $\omega=90°$, since the aperture 34 of the tubular component 29 of the gas-suctioning device 28 is at a position immediately downstream from the sample rod 23 and the sample S and higher than the $\omega$ axis, the gas downstream from the sample rod 23 flows into the aperture 34 immediately after forming a large curvature, and turbulence is suppressed. Even when turbulence occurs, the turbulence is immediately suctioned from the aperture 34. In other words, the gas flow is immediately suctioned in the direction away from the sample S. Ice is therefore prevented from forming on and around the sample S, and stable, highly reliable data for the sample S can be obtained.

Since the center G of the aperture 34 is eccentric with respect to the $\omega$ axis in the present embodiment, the gas flow discharged from the discharge nozzle 26 can be actively suctioned in a large curvature via the aperture 34. Since the front surface of the tubular component 29 is tilted in alignment with the extension direction of the sample rod 23, the gas flow from the discharge nozzle 26 can smoothly flow into the aperture 34, and turbulence and consequent ice formation and adhesion can be effectively prevented. The guide plate 33 is further provided on the lower portion of the aperture 34 in the present embodiment, and the guide plate 33 is tilted in substantially the same plane as the aperture 34. The gas flow in the blowing direction D can therefore be smoothly guided into the aperture 34 by the guide plate 33, and the effect of turbulence on the sample S can thereby be even further reduced.

The situation in which turbulence occurs downstream from the sample rod 23 and ice adheres to and around the sample S is thought to correspond to a situation in which the gas flow contacts the sample rod 23 before contacting the sample S. This situation occurs when the angle, in the direction of the gas flow, between the extension direction of the sample rod 23 and the gas blowing direction D is 90° or less, i.e., acute. More specifically, this situation occurs between the time that the ω angle of the sample S is ω=90°, as shown in FIG. 4A and the time that ω=0°, as shown in FIG. 5A. Suctioning the gas flow through the aperture 34 as shown in FIG. 7 in this case facilitates suppression of turbulence and complete recovery of any turbulence that does occur before the turbulence adversely affects the sample S. This suctioning also overcomes formation and adhesion of ice.

Figure 8:
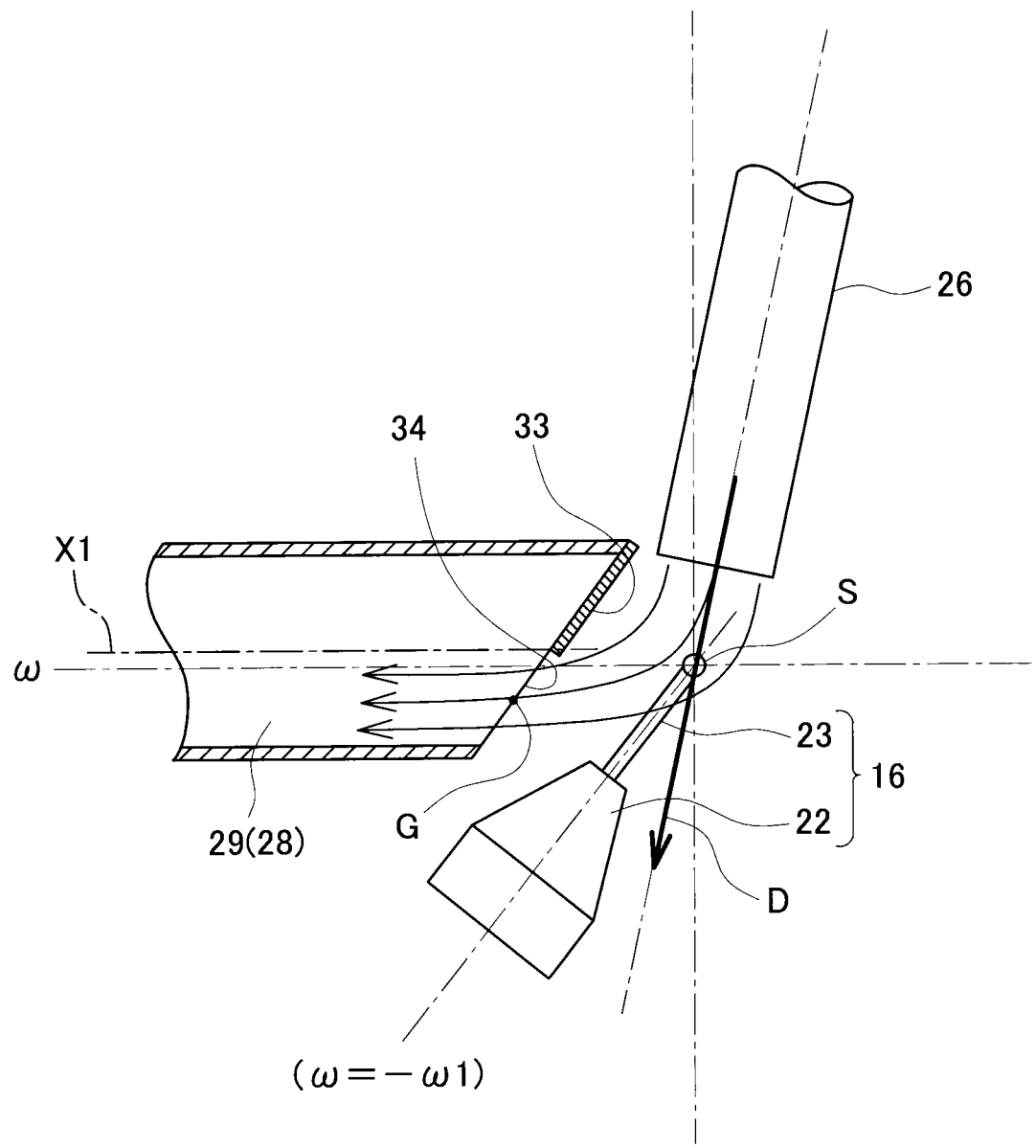
FIG. 8 is a schematic view showing state of flow of the cooling gas in the state (ω=−1° of FIG. 6B.

When the sample S and the sample rod 23 are in the lower position at which ω=−ω1 as shown in FIG. 6A, the gas suctioned into the aperture 34 of the tubular component 29 of the gas-suctioning device 28 after flowing out from the discharge nozzle 26 is as shown schematically in FIG. 8. Specifically, when ω=−ω1, the sample rod 23 supporting the sample S enters the gas flow at an upward-sloping tilt. At this time, speaking of the plane at a right angle to the direction D in which gas is blown by the discharge nozzle 26, this plane first touches the sample S and then touches the sample rod 23. In other words, the gas flow contacts the sample rod 23 after contacting the sample S. At this time, even when turbulence has formed on the downstream side of the sample rod 23, this turbulence has no effect on the sample S, and almost no ice adheres to or around the sample S.

In the case that the sample S and the sample rod 23 are at ω=−ω1, the aperture 34 of the tubular component 29 of the gas-suctioning device 28 is positioned lower than the ω axis. The gas flow from the discharge nozzle 26 is therefore smoothly suctioned in a small curvature through the aperture 34, rather than being forcefully suctioned in a large curvature such as in the case shown in FIG. 7. In the case considered here in which ω=−ω1, since the gas flow contacts the sample rod 23 after contacting the sample S, turbulence that occurs downstream from the sample rod 23 has little effect on the sample S, and therefore no problems arise from a gentle gas suctioning such as shown in FIG. 8.

The situation in which the gas flow from the discharge nozzle 26 contacts the sample rod 23 after contacting the sample S occurs in the case that the angle, in the direction of the gas flow, between the extension direction of the sample rod 23 and the gas blowing direction D is greater than 90°, i.e., obtuse. More specifically, this situation occurs between the time that the ω angle of the sample S is ω=0°, as shown in FIG. 5A and the time that ω=−ω1, as shown in FIG. 6A. In this case, there are no risks of adhesion of ice formed by turbulence, even when the gas flow is not strongly suctioned by the gas-suctioning device 28.

As described above, in the present embodiment, the discharge nozzle 26 discharges low-temperature gas downward from above in FIG. 1, and the sample rod 23 rotates about the ω axis so as to describe a conical surface. Therefore, between the ω angles of 90° to 0° about the ω axis, a situation occurs in which the gas discharged from the discharge nozzle 26 contacts the sample S after contacting the sample rod 23. In this case, there is a risk of ice adhering to or around the sample S due to the effect of turbulence downstream from the sample rod 23. However, in the present embodiment, since the aperture 34 for gas suctioning is provided in the vicinity of the sample S, and the gas flow that has passed over the sample rod 23 is immediately suctioned, turbulence can be suppressed, and any turbulence that does occur can be immediately separated from the sample S. Ice can therefore be prevented from forming on and adhering to the sample.

In the present embodiment, since the tubular component 29 of the gas-suctioning device 28 moves integrally with the sample support 16, the tubular component 29 and the sample support 16 do not collide with each other. The aperture 34 at the distal end of the tubular component 29 can therefore be brought to the immediate vicinity of the sample S. Since the distal end surface of the tubular component 29, formed by the aperture 34 and the guide plate 33, is tilted in alignment with the extension direction of the sample rod 23, turbulence can be precisely prevented. Furthermore, since the center G of the aperture 34 of the tubular component 29 is offset, i.e., eccentrically disposed, with respect to the ω axis, the position and area of the gas-blowing aperture 34 with respect to the sample S can be adjusted so that turbulence can be efficiently recovered.

In the present embodiment as shown in FIG. 1, the gas-suctioning device 28 is detachably attached to the ω rotation substrate 13 by the attachment structure 32. The gas-suctioning device 28 can therefore be used when needed, and the gas-suctioning device 28 can be removed when not needed. The position of the gas-suctioning device 28 can also be freely adjusted.

(Second Embodiment of the Sample Cooling Apparatus)

Figure 9:
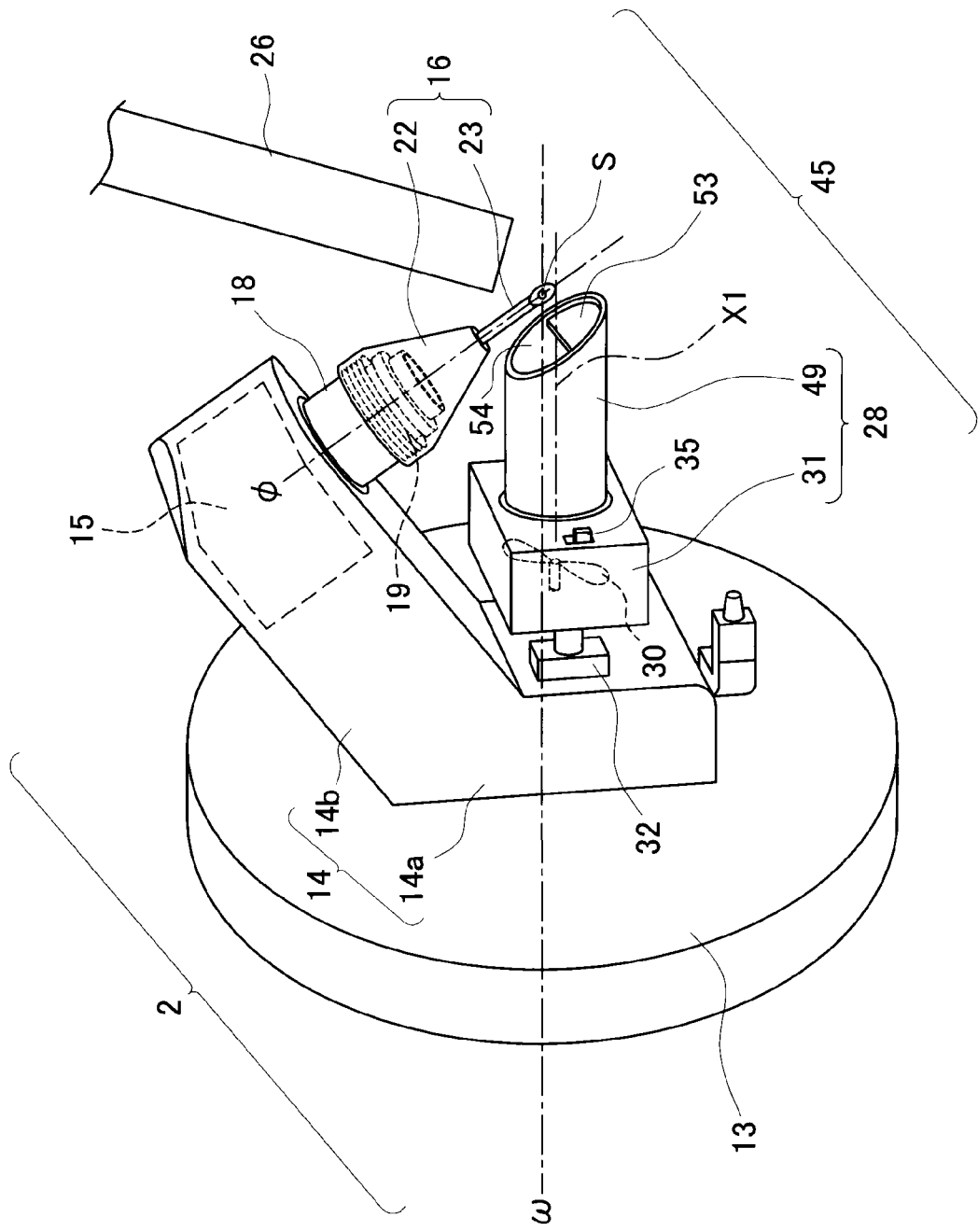
FIG. 9 is a perspective view showing another embodiment of the sample support system and sample cooling apparatus as main components of the X-ray diffractometer of the present invention.

FIG. 9 shows another embodiment of the sample cooling apparatus according to the present invention. The sample cooling apparatus 45 of the present embodiment differs from the sample cooling apparatus 5 shown in FIG. 2 in that a modification is made to a tubular component 49 of the gas-suctioning device 28. Members of the embodiment shown in FIG. 9 that are the same as in the embodiment shown in FIG. 2 are referred to by the same reference symbols, and no further description of such components will be given.

In the sample cooling apparatus 5 shown in FIG. 2, the guide plate 33 provided to the distal end surface of the tubular component 29 of the gas-suctioning device 28 is formed so as to extend beyond the peripheral edge of the distal end surface of the tubular component 29. In the present embodiment shown in FIG. 9, however, a guide plate 53 is provided inside the peripheral edge of the distal end surface of the tubular component 49. This configuration makes it possible to change the direction of flow of the gas flow that comes away from the discharge nozzle 26, flow over the sample S, and is suctioned into an aperture 54.

(Third Embodiment of the Sample Cooling Apparatus)

Figure 10:
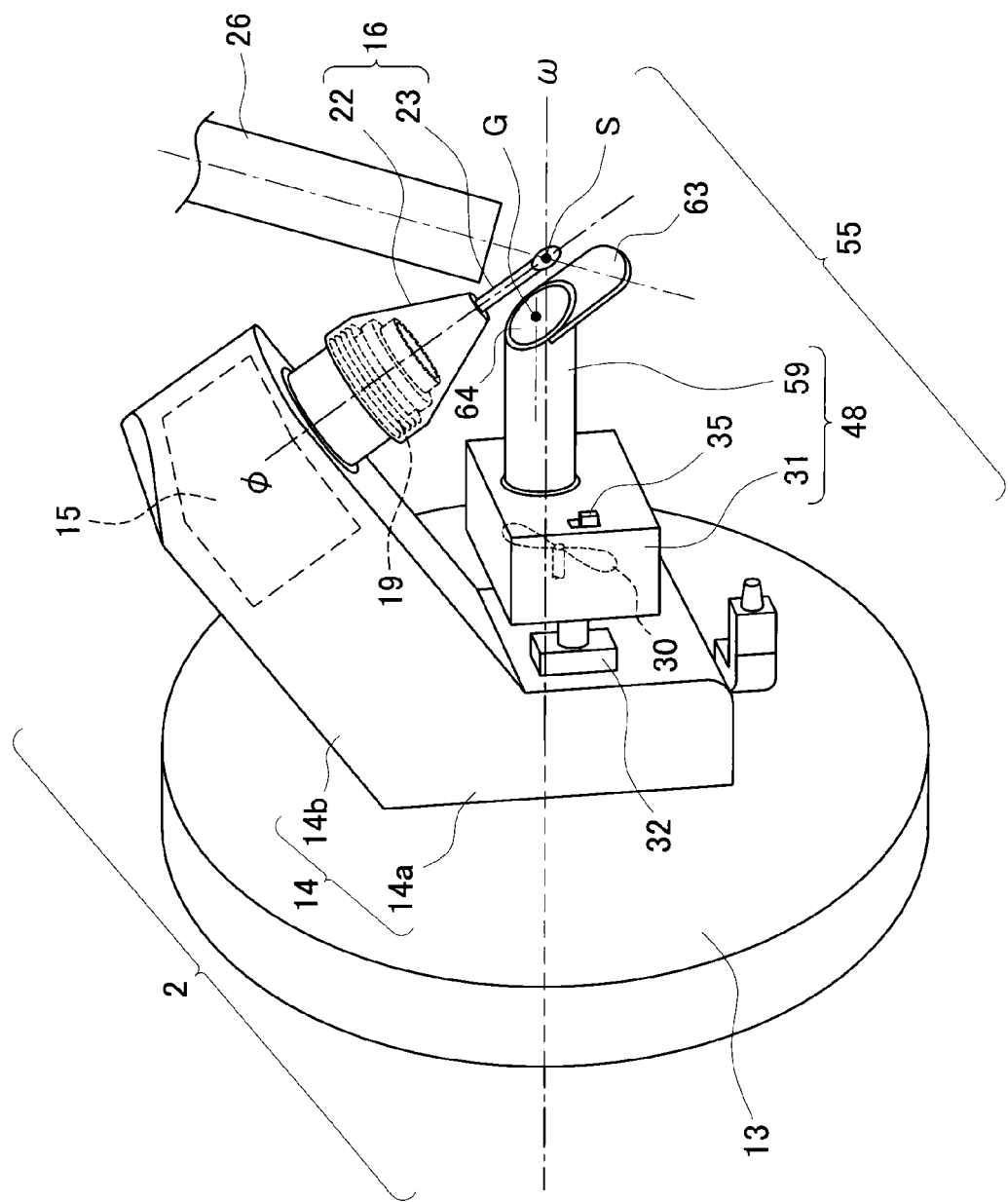
FIG. 10 is a perspective view showing yet another embodiment of the sample support system and sample cooling apparatus as main components of the X-ray diffractometer of the present invention.
Figure 11:
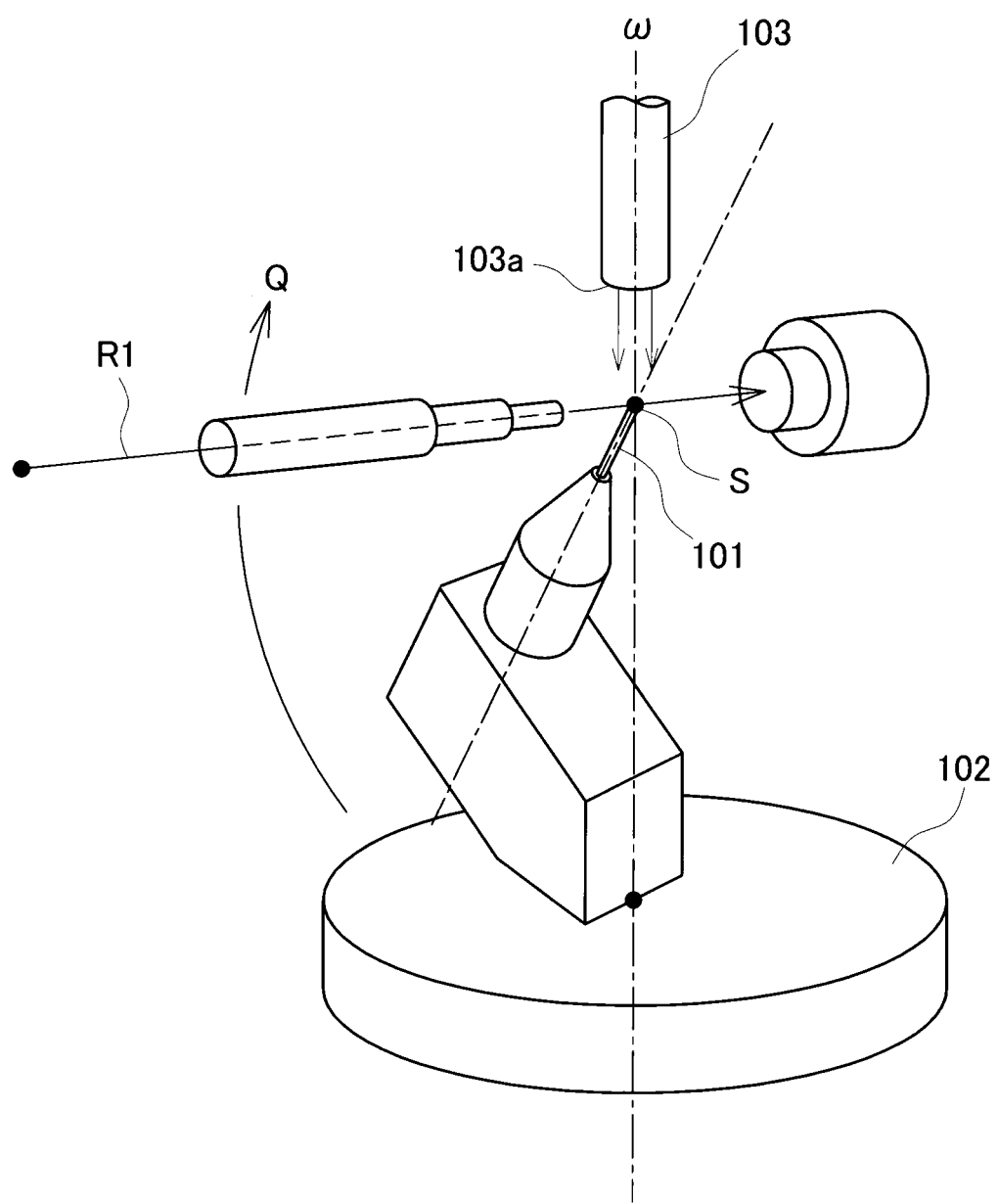
FIG. 11 is a perspective view showing an example of a conventional X-ray diffractometer.

FIG. 10 shows a still another embodiment of the sample cooling apparatus according to the present invention. The sample cooling apparatus 55 of the present embodiment differs from the sample cooling apparatus 5 shown in FIG. 2 in that a modification is made to a gas-suctioning device 48. Members of the embodiment shown in FIG. 10 that are the same as in the embodiment shown in FIG. 2 are referred to by the same reference symbols, and no further description of such components will be given.

In the sample cooling apparatus 5 shown in FIG. 2, the aperture 34 is formed in a portion, i.e., in substantially half the area, of the distal end surface of the tubular component 29. The portion of the distal end surface other than the aperture 34 forms the guide plate 33. In the present embodiment shown in FIG. 10, however, an aperture 64 is formed in the entire area or in substantially the entire area of the distal end surface of a tubular component 59, and a guide plate 63 is connected to a lower portion of an external peripheral surface of the distal end surface. The guide plate 63 may be connected by bonding, welding, screws, or any other means of connection.

In the present embodiment as well, the center G of the aperture 64 is shifted, i.e., eccentrically disposed, with respect to the ω axis. The aperture 64 and the guide plate 63 are also continuous with no gap therebetween, and form a single substantially flat surface. The gas flow coming away from the discharge nozzle 26 is actively suctioned by the aperture 64 in the present embodiment as well. The guide plate 63 also enables a smooth and stable gas flow to be formed.

(Other Embodiments)

The present invention is described above using preferred embodiments, but the present invention is not limited by these embodiments and can be modified in various ways within the scope of the invention as recited in the claims.

For example, the sample cooling apparatus of the present invention may be applied in an X-ray diffractometer other than a single crystal structure analysis device. The guide plate 33 (FIG. 2) and the guide plate 53 (FIG. 9) may also be omitted insofar as the desired gas flow can be obtained merely through the aperture 34 (FIG. 2) and aperture 54 (FIG. 9). The gas-suctioning part 31 may also have a suction structure configured differently than the suction structure which uses the fan 30.

(Description of Reference Numerals)

1.X-ray diffractometer, 2.Sample support system, 3.Incidence optical system, 4.Light-receiving system, 5.Sample cooling apparatus, 8.X-ray generation device, 9.Monochromator, 10.Collimator, 11.Two-dimensional X-ray detector, 13.ω rotation substrate, 14.Arm component, 14a.Base part, 14b.Protruding part, 15.φ-axis drive system, 16.Sample support, 17.ω-axis drive system, 18.Output shaft, 19.Helical screw, 22.Base, 23.Sample rod(Sample-supporting component), 26. Discharge nozzle, 27.Low-temperature gas feeding device, 28.Gas-suctioning device(Gas-suctioning means), 29.Tubular component, 30.Fan, 31.Gas-suctioning part, 32.Attachment structure(magnet), 33.Guide plate, 34.Aperture, 35.Starting switch, 45.Sample cooling apparatus, 48.Gas-suctioning device(Gas-suctioning means), 49.Tubular component, 53.Guide plate, 54.Aperture, 55.Sample cooling apparatus, 59.Tubular component, 63.Guide plate, 64.Aperture, C. Conical surface, D. Blowing direction, F. X-ray source, G. Center of the aperture 34, S. Sample, P0,P1, P2. Positions through which the sample support 16 can move, R1.Incident X-rays, R2. Diffracted X-rays, X0. X-ray optical axis X0, X1. Axial center, δ1.Offset amount, δ2.Offset amount from the ω axis,

What is claimed is:

1. A sample cooling apparatus for cooling a sample, the apparatus being used in an X-ray diffractometer for rotating, about an ω axis, a sample supported by a sample-supporting component in order to change an angle at which X-rays impinge on the sample, directing X-rays on the sample, and detecting X-rays coming away from the sample using an X-ray detector, the sample cooling apparatus for the X-ray diffractometer comprising:

cooling-gas-blowing means for blowing a cooling gas on the sample; and gas-suctioning means for suctioning, via an aperture, gas that has passed over the sample, wherein:

the sample-supporting component moves when rotated about the ω axis so as to form a conical surface having the sample as a vertex;

the cooling-gas-blowing means is provided so that the direction in which the sample-supporting component extends and the direction in which gas is blown by the cooling-gas-blowing means form a state of being an acute angle of equal to or less than 90°;

the gas-suctioning means suctions the gas so that a path of the gas having contacted the sample-supporting component bends when the direction in which the sample-supporting component extends and the direction in which gas is blown by the cooling-gas-blowing means form the acute-angle state; and the gas-suctioning aperture of the gas-suctioning means integrally rotates about the ω axis together with the sample.

2. The sample cooling apparatus for an X-ray diffractometer according to claim 1, wherein the aperture is formed at a distal end of a tubular component; and the central axis of the tubular component extends parallel to the ω axis.

3. The sample cooling apparatus for an X-ray diffractometer according to claim 2, wherein the distal end of the tubular component has an incline that follows the direction in which the sample-supporting component extends.

4. The sample cooling apparatus for an X-ray diffractometer according to claim 3, wherein the aperture is formed at a distal end surface of the tubular component; a guide plate is attached to the distal end of the tubular component; the center of the aperture is disposed eccentrically with respect to the ω axis; and the guide plate is connected to the aperture.

5. The sample cooling apparatus for an X-ray diffractometer according to claim 3, wherein the aperture is formed on a portion of a distal end surface of the tubular component; a portion of the distal end surface of the tubular component other than the aperture is a guide plate; and the center of the aperture is disposed eccentrically with respect to the ω axis.

6. The sample cooling apparatus for an X-ray diffractometer according to claim 4, wherein the center of the aperture is eccentrically disposed toward the sample-supporting component location side of the ω axis.

7. The sample cooling apparatus for an X-ray diffractometer according to claim 6, comprising an ω rotation substrate on which the sample-supporting component is supported, the substrate rotating integrally with the sample-supporting component about the ω axis; and the gas-suctioning means has:

a gas-suctioning part integrally provided to the tubular component; and an attachment structure by which the mutually integrated tubular component and gas-suctioning part are detachably attached to the ω rotation substrate.

8. The sample cooling apparatus for an X-ray diffractometer according to claim 7, wherein the ω axis extends in a horizontal direction; and the direction in which gas is blown by the gas-blowing means is a direction oriented downward from above.

9. The sample cooling apparatus for an X-ray diffractometer according to claim 8, wherein the X-ray diffractometer has a ω-axis drive system for causing the sample to rotate about the ω axis, and a φ-axis drive system for causing the sample-supporting component to rotate about a central axis thereof;

the impingement angle at which X-rays impinge on the sample is continuously caused to oscillate and change by the ω-axis drive system;

the sample is rotated in a stepwise manner by the φ-axis drive system; and

X-rays are made to impinge in individual X-ray impingement angle positions and in individual angular positions around the φ axis, and X-rays coming away from the sample are detected by the X-ray detector.

10. An X-ray diffractometer for rotating, about an ω axis, a sample supported by a sample-supporting component in order to change an angle at which X-rays impinge on the sample, directing X-rays on the sample, and detecting X-rays coming away from the sample using an X-ray detector; the X-ray diffractometer comprising the sample-cooling apparatus according to claim 9.

11. An X-ray diffractometer for rotating, about an ω axis, a sample supported by a sample-supporting component in order to change an angle at which X-rays impinge on the sample, directing X-rays on the sample, and detecting X-rays coming away from the sample using an X-ray detector; the X-ray diffractometer comprising the sample-cooling apparatus according to claim 3.

12. An X-ray diffractometer for rotating, about an ω axis, a sample supported by a sample-supporting component in order to change an angle at which X-rays impinge on the sample, directing X-rays on the sample, and detecting X-rays coming away from the sample using an X-ray detector; the X-ray diffractometer comprising the sample-cooling apparatus according to claim 4.

13. An X-ray diffractometer for rotating, about an ω axis, a sample supported by a sample-supporting component in order to change an angle at which X-rays impinge on the sample, directing X-rays on the sample, and detecting X-rays coming away from the sample using an X-ray detector; the X-ray diffractometer comprising the sample-cooling apparatus according to claim 6.

14. An X-ray diffractometer for rotating, about an ω axis, a sample supported by a sample-supporting component in order to change an angle at which X-rays impinge on the sample, directing X-rays on the sample, and detecting X-rays coming away from the sample using an X-ray detector; the X-ray diffractometer comprising the sample-cooling apparatus according to claim 8.

* * * * *